(12) United States Patent
Howdle et al.

(10) Patent No.: US 6,414,050 B1
(45) Date of Patent: Jul. 2, 2002

(54) BIOFUNCTIONAL POLYMERS PREPARED IN SUPERCRITICAL FLUID

(75) Inventors: Steven Melvyn Howdle, Nottingham (GB); Vladimir Popov, Moscow (RU)

(73) Assignee: University of Nottingham, Nottingham (GB)

( * ) Notice: Subject to any disclaimer, the term of this patent is extended or adjusted under 35 U.S.C. 154(b) by 0 days.

(21) Appl. No.: 09/423,306

(22) PCT Filed: May 6, 1998

(86) PCT No.: PCT/GB98/01325

§ 371 (c)(1),
(2), (4) Date: Jan. 10, 2000

(87) PCT Pub. No.: WO98/51347

PCT Pub. Date: Nov. 19, 1998

(30) Foreign Application Priority Data

May 10, 1997 (GB) ............................................... 9709561
Jan. 19, 1998 (GB) ............................................... 9800936

(51) Int. Cl.⁷ ............................ C08K 3/00; A61K 51/00
(52) U.S. Cl. .................. 523/105; 424/1.29; 424/9.322; 424/469
(58) Field of Search ................................. 523/105, 111, 523/113, 172; 521/56, 57; 424/497, 405, 408, 1.29, 9.822, 409, 419, 464, 469, 474, 475, 489, 490

(56) References Cited

U.S. PATENT DOCUMENTS

| 4,598,006 A | 7/1986 | Sand | 424/81 |
|---|---|---|---|
| 5,290,827 A | 3/1994 | Shine | 523/340 |
| 5,340,614 A | 8/1994 | Perman et al. | 427/2.24 |
| 5,548,004 A | 8/1996 | Mandel et al. | 523/342 |
| 5,679,737 A * | 10/1997 | DeSimone et al. | 524/529 |
| 5,766,637 A * | 6/1998 | Shine et al. | 424/497 |
| 6,248,363 B1 * | 6/2001 | Patel et al. | 424/422 |

FOREIGN PATENT DOCUMENTS

| EP | 464163 B1 * | 4/1995 |
|---|---|---|
| WO | WO91/09079 | 6/1991 |
| WO | WO 99/19085 A1 * | 4/1999 |

* cited by examiner

Primary Examiner—Edward J. Cain
Assistant Examiner—Kataryna W. Ree
(74) Attorney, Agent, or Firm—Jacobson Holman, PLLC

(57) ABSTRACT

Compositions comprising an admixture of a biofunctional polymer substrate and a biofunctional material substrate adapted for use in or in association with the human or animal body, cultivated or uncultivated living matter and methods for making and using thereof are disclosed. The biofunctional material substrate retains bioactivity in the admixture. As disclosed, the compositions may be made by a process which comprises contacting a mixture of the substrates or their precursors with a supercritical fluid under supercritical conditions of reduced viscosity to plasticise and swell the biofunctional polymer substrate and under conditions of physical blending to distribute the biofunctional material substrate throughout the biofunctional polymer substrate, and releasing the supercritical fluid under subcritical conditions. Also disclosed are biofunctional polymer matrices and methods of making and using thereof.

26 Claims, 3 Drawing Sheets

BIOFUNCTIONAL POLYMERS PREPARED IN SUPERCRITICAL FLUID

Figure 1A:
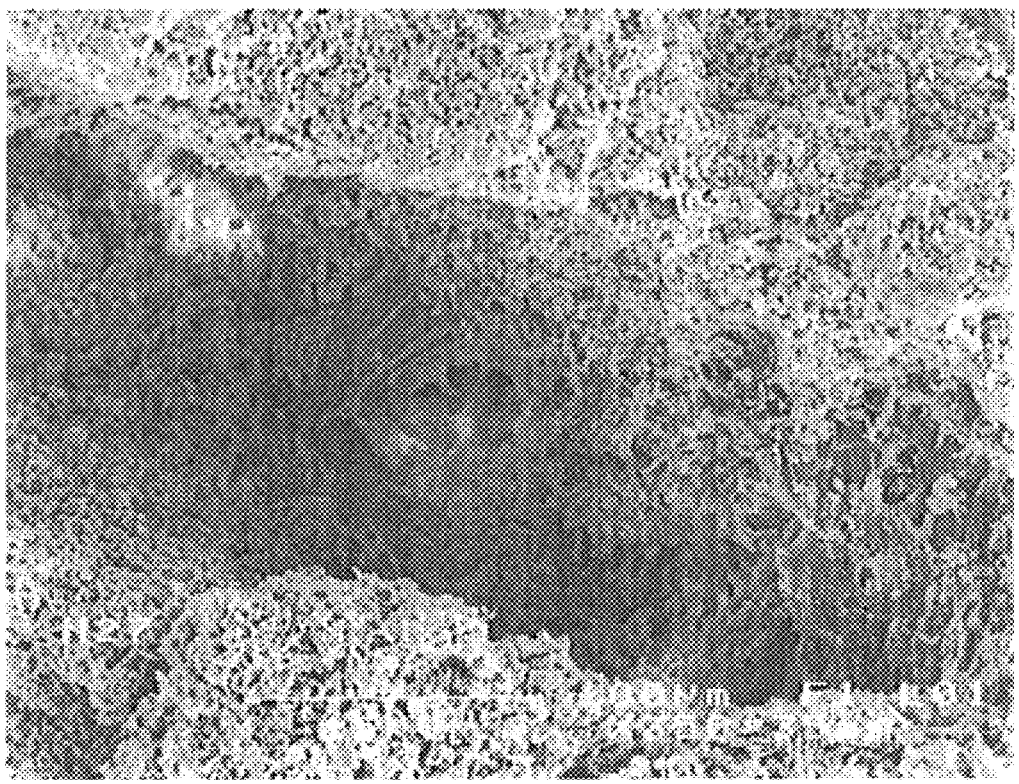

The present invention relates to a process for the preparation of a biofunctional polymer composition comprising biofunctional material adapted for use in or in association with a biolocus such as the human or animal body or cultivated or uncultivated living matter, the polymer compositions, and apparats for the preparation thereof. More particularly the present invention relates to the process, the polymer compositions, and their polymer compositions, and apparatus for the preparation thereof, wherein biofunctional material is adapted for release of biofunctional material into the human or animal body or living matter and/or adapted for insertion into human or animal host structures.

The use of supercritical fluids in the production of polymers as a swelling, foaming or purification agent is known from various sources. Supercritical fluid serves to increase resin mobility thereby improving mixing and processing, to reduce the polymer glass transition temperature by swelling, and enabling processing at lower temperatures, and acts as a solvent for impurities (including unreacted monomer and residual conventional solvents) which may be removed during the processing to give high purity products. Moreover the fluid can be used to aerate the polymer by transition to non critical gaseous state whereby a porous material may be obtained. Supercritical fluid has found application in incorporation of dyes and other inorganic materials which are insoluble in the supercritical fluid, for example inorganic carbonates and oxides, into polymers with a good dispersion to improve quality, in particular dispersion in products such as paints for spray coating and the like.

Polymers have also been used in biomedical applications to develop materials in which biocompatibility can be influenced to promote favourable tissue responses whilst also producing materials with acceptable mechanical and surface properties. Biofunctional composite materials e.g. calcium hydroxyapatite dispersed in various polymers are well established for orthopaedic, dental and other applications. These materials are prepared with very high loadings of biofunctional inorganic solid, of up to 80%, in the form of a powder, and a composite is formed either by vigorous mixing of the powdered material into the solid or molten polymer, or by polymerisation of the monomers in the presence of suspended inorganic powders. In both cases, the material becomes entrapped within the polymer matrix. Particle size is selected for higher mechanical strength (ca. 25 m) or surface polishing finishing (ca. 1–8 m). These methods for preparation however are prone to insufficient and uncontrolled mixing of material leading to large aggregate formation whereby the composite is prone to fracture and may not be suitable for commercial processing.

The processes have moreover found limited application in incorporating materials which are limited by solubility constraints and sensitivity to process conditions into polymers.

Accordingly there is a need for a process for the preparation of biofunctional polymers having the desired properties for commercial processing and for use in or in association with the human or animal body or living matter as a biofunctional material release agent or a toxicity shielding or barrier agent, or as an implant into a human or animal host structure such as bone or cartilage, dental and tissue structures into which they are surgically implanted for orthopaedic bone and implant, prosthetic, dental filling or restorative applications and the like.

Moreover there is a need for biofunctional polymers having the desired mechanical properties both for commercial processing and for implant into a human or animal host structure such as bone or cartilage, dental and tissue structures into which they are surgically implanted for orthopaedic bone an implant, prosthetic, dental filling or restorative applications and the like.

We have now surprising found that the properties of supercritical fluids may be employed to further advantage in the preparation of biofunctional polymers for the improved processing and quality thereof, in a process which is notably independent of solubility constraints and sensitivity of biofunctional materials.

Accordingly in a first aspect of die invention there is provided a process for the preparation of a composition comprising a biofunctional polymer substrate and biofunctional material substrate adapted for use in or in association with the human or animal body, cultivated or uncultivated living matter, wherein the biofunctional material substrate is optionally substantially insoluble in the polymer substrate and/or a supercritical fluid, wherein the process comprises contacting a mixture of the substrates or their precursors with a supercritical fluid under supercritical conditions and conditions of reduced viscosity and physical blending to plasticise and swell the polymer and distribute the biofunctional martial substrate throughout the polymer, and releasing the fluid under subcritical conditions, wherein the substrates are adapted to be isolated in form of a solid admixture comprising the biofunctional material substrate in substantially unchanged chemical form, and optionally in substantially unchanged physical form.

Reference herein to precursors of polymer and/or material substrates, is to components thereof which may be combined in the process of the invention, together with supercritical fluid under the defined process conditions, whereby the precursors react to form the substrate(s) in situ. For example functional or non functional component precursors of the biofunctional material may be simultaneously reacted and admixed according to the process of the invention.

Reference herein to a solid admixture is to any desired morphology. For example the biofunctional material substrate may be encapsulated by the biofunctional polymer substrate in the form of a coating, resembling a particulate morphology or may be distributed throughout the biofunctional polymer substrate resembling a (co-)continuous morphology.

In some cases the transition from coated or encapsulated particles to distributed mixtures is merely a gradation of order of magnitude. whereby particles. pellets, monoliths and the like may effectively comprise a plurality of biofunctional material particles independently coated with or encapsulated by a continuous phase of polymer. This is conveniently termed particulate morphology.

It has surprisingly been found that according to the present invention a process is provided which may be suited to the preparation of composition comprising any biofunctional polymer and material substrams, irrespective of the chemical or physical nature thereof, whereby classical processing requirements such as matching solubilities, melt extrusion, mechanical mixing and the like to obtain a suitable blend are found to be not essential to the successful processing of the composition avoiding solvent poisoning and monomer residues.

The process may therefore be carried out in the presence or absence of additional carriers or solvents, and by selection of biofunctional material substrate which is optionally insoluble in the polymer substrate and/or the supercritical fluid.

Preferably however, where it is desired to obtain a composition comprising a solid admixture comprising the biofunctional material substrate in substantially unchanged chemical and physical form, the process is operated in the substantial absence of the additional carrier or solvent, and with use of biofunctional material substrate which is substantially insoluble in the polymer substrate and the supercritical fluid. By this means it is found that biofunctional material in the form to provide the required bioactivity or like performance, for processing thereof to form the composition, will retain that form in the processed composition.

Preferably the process is carried out in the substantial absence of solvent or carrier, by mixing of solid phase material substrate into fluid or solid phase polymer and fluid phase supercritical fluid, whereby the absence of surface tension associated with liquid phase biofunctional material enables excellent dispersion It is a particular feature of the process of the present invention that conditions of reduced viscosity and physical blending are selected to provide the required plasticisation, swelling and distribution. Conditions will be selected according to the substrate being employed, and the state of the polymer/material mixture in supercritical fluid will be monitored to detect appropriate states of plasticisation and swelling.

Preferably the conditions are controlled throughout to ensure density matching of fluid and polymer components which, together with efficient physical blending or mixing, leads to homogenous mixing of biofunctional material, Blending may be by physical mixing, pumping or otherwise impregnation or diffusion of fluid throughout the polymer/material system.

Preferably blending and reduced viscosity are achieved by agitation with associated shear thinning, for example with aeration or fluidising gas flow, stirring or the like, according to known techniques, more preferably according to the process of U.S. Pat. No. 5,548,004 (Ferro Corp) the contents of which are incorporated herein by reference.

It is a particular advantage of the process of the present invention that the arrainment of this polymer mixture state dispenses with the need to provide solvents or polymer melts in order to combine components for mixing thereof, and moreover dispenses with the need to remove carrier or solvent which may be a source of contamination, toxicity, deactivation or the like.

The components of the polymer composition may be combined in any desired order, prior to, or during application of supercritical conditions.

The fluid may be present in any effective amount with respect to the polymer composition, Preferably the substrates are immersed in or contacted with the fluid in a batchwise process.

Transition from supercritical to subcritical conditions may be achieved in situ, by depressurising a pressure vessel in which the process is carried out, and simultaneously or otherwise ceasing mixing, whereby a foamed monolithic block of polymer is obtained. Alternatively the contents of pressure vessel in which the process is conducted may be discharged into a second pressure vessel at lower pressure whereby a homogeneous porous powder of polymer as hereinbefore defined is obtained by known means.

The process may be controlled in manner to determine the dimensions and void fraction of micro and macro pores.

Suitably the system is rendered non-fluid prior to or subsequent to release of fluid in the third step, in order to retain the porous structure induced by the fluid.

In some cases it may be desirable to introduce an initiator or accelerator to indicate (partial) curing prior to and/or subsequent to release of fluid, and initiation may be simultaneous with introduction or may be delayed, activated by increase in temperature. Alternatively a spray drying step may be employed in place of the curing step prior to or simultaneously with release of the fluid. In this case a posts may be employed. This may have advantages in terms of ease of manufacturing and simplicity of apparatus employed.

Further processing of the polymer, for example additional extraction with super critical fluid as known in the art or with other extractants, post-polymerisation and cross-linking, may be subsequently performed as required and as known in the art.

The process of the invention may be conducted with use of any known techniques commonly employed in the preparation of polymers.

The polymer may be selected from any known polymer which is suited for introduction into or association with the human or animal body or living matter in non-toxic manner. Suitable polymer materials are selected from synthetic biodegradable polymers as disclosed in "Polymeric Biomaals" em Severian Dumitriu, ISBN 0-82478969-5, Publ. Mael Dekker, N.Y., USA, 1994, synthetic non-biodegradable polymers; and natural polymers. Preferably the polymer is selected from homopolymers, block and random copolymers, polymeric blends and composites of monomers which may be straight chain, (hyper) branched or cross-linked Polymers may include but are not limited to the following which are given as illustration only.

Synthetic biodegradable polymers may be selected from:

Polyesters including poly(lactic acid), poly(glycolic acid), copolymers of lactic and glycolic acids copolymers of lactic and glycolic acid with poly(ethylene glycol), poly(e-caprolactone), poly(3-hydroxybutyrate), poly (p-dioxanone), poly(propylene fumarate);

Poly (ortho esters) including Polyol/diketene acetals addition polymers as described by Heller in: ACS Symposium Series 567,292–305, 1994:

Polyanhydrides including poly(sebacic anbydride) (PSA), poly(carboxybisbarboxyphenoxyphenoxyhexan) (PCP), poly[bis(p-carboxyphenoxy) methane] (PCPM), copolymers of SA, CPP and CPM, as described by Tamada and Langer in Journal of Biomaterial Science Polymer Edition, 3, 315–353,1992 and by Domb in Chapter 8 of the Handbook of Blodegradable Polymers, ed Domb A. J. and R. M., Harwood Academic Publishers;

Poly(amino acids);

Poly(pseudo amino acids) including those described by James and Kohn in pages 389–403 of Controlled Drug Delivery Challenges and Straegies, American Chemical Society, Washington D.C.;

Polyphosphuenes including derivatives of poly[(dichloro) phosphazene], poly[(organo) phosphazenes], polymers described by Schacht in Biotechnology and Bioengineering, 52, 102–108, 1996: and Azo polymers Including those described by Lloyd in International Journal of Pharmaceutics. 106,255–260, 1994.

Synthetic Non-biodegrdable Polymers may be selected from:

Vinyl polymers including polyethylone. poly(ethylene-co-vinyl acetate), polypropylene poly(vinyl chloride), poly (vinyl acetate), poly(vinyl alcohol) and copolymers of vinyl alcohol and vinyl acetate, poly(acrylic acid) poly (medacrylic acid), polyacrylamides, polymethacrylamides, polyaxrylates, Poly(ethylene glycol), Poly(dimethyl siloxane). Polyurethanes, Polycarbonates, Polystyrene and derivatives, Natural Polymers may be selected from carbohydraes, polypeptides and proteins including:

Starch, Cellulose and derivatives including ethylcellulose, methylcellulose, ethylhydroxyetbylcellulose, sodium carboxyniethylcellulose; Collagen; Gelatin; Dextran and derivatives; Alginates; Chitin; and Chitosan:

Preferably a non biodegradable polymer is selected from polymers such as ester urethanes or epoxy, bis-maleimides, metcrylates such as methyl or glycidyl methacrylate, tri-methylene carbonate di-methylene tri-methylene carbonate; biodegradable syntetic polymers such as glycolic acid, glycolide, lactc acid, lacide, p-dioxanone, dioxepanone, alkylene oxalates and caprolactones such as gamma-caprolactone.

The polymer may comprise any additional polymeric components having performance enhancing or controlling effect, for example determining the degree and of cross-linking for improved permeability by bodily fluids or pharmaceutically effective agent, flexural and general mechanical properties.

The biofunctional martial may be selected from any materials adapted to perform a fusion on a desired biolocus comprising or otherwise associated with living matter, as hereinbefore defined. A biofunctional material may be bioactive, bioinert, biocidal or the like.

Preferably a biofunctional material is adapted to induce growth, strengthen, supplement or enhance a desired human, animal or living matter host structure, or combat or protect against threats to the host structure or to the human or animal body in general. The material may be selected from any inorganic or organic material which is optionally substantially insoluble in supercritical fluid, in either or both of its non critical and supercritical states.

More specifically the biofunctional material includes but is not limited to the following examples typically classed as (pharmaceutical) drugs and veterinary products; agrochemicals as pest and plant growth control agents; human and animal health products; human and animal growth promoting, structural, or cosmetic products including products intended for growth or repair or modelling of the skeleton, organs, dental structure and the like; absorbent biofunctional materials for poisons, toxins and the like.

Pharmaceuticals and veterinary products, i.e. drugs, may be defined as any pharmacologically active compounds that alter physiological processes with the aim of treating, preventing, curing, mitigating or diagnosing a disease.

Drugs may be composed of inorganic or organic molecules, peptides, proteins, enzymes, oligosaccharides, carbohydrates, nucleic acids and the like.

Drugs may include but not be limited to compounds acting to treat the following;

Infections such as antiviral drugs. antibacterial drugs, antifungal drugs, antiprotozal drugs, anthelmintics, Cardiovascular system such as positive inotopic drugs, diuretics, anti-arrhythmic drugs, beta-adrenoceptor blocking drugs, calcium channel blockers, sympathomimetics, anticoagulants, antplatelet drugs, fibrinolytic drugs, lipid-lowering drugs;

Gastro-intestinal system agents such as antacids, antispasmodics, ulcer-healing, drugs, anti-diarrhoeal drugs, laxatives, central nervous system, hypnotics and anxiolytics, antipsychotics, antidepressants, central nervous system stimulants, appetite suppressants, drugs used to treat nausea and vomiting, analgesics, antiepileptics, drugs used in parkinsonism, drugs used in substance dependence;

Malignant disease and immunosuppresion agents such as cytotoxic drugs, immune response modulators, sex hormones and antagonists of malignant diseases;

Respiratory system agents such as bronchodilators, corticosteroids, cromoglycate and related therapy, antihistamines, respiratory stimulants, pulmonary surfactants, systemic nasal decongestants;

Musculoskeletal and joint diseases agents such as drugs used in rheumatic diseases, drugs used in neuromuscular disorders; and Immunological products and vaccines.

Agrochemicals and crop protection products may be defined as any pest or plant growth control agents, plant disease control agents, soil improvement agents and the like. For example pest growth control agents include insecticides, miticides, rodenticides, molluscicides, slugicides, vermicides (nematodes, anthelmintics), soil fumigants, pest repellants and attractants such as pheromones etc, chemical warfare agents, and biological control agents such as microorganisms, predators and natural products;

plant growth control agents include herbicides, weedicides, defoliants, dessicants, fruit drop and set controllers, rooting compounds, sprouting inhibitors, growth stimulants and retardants, moss and lichen controllers and plant genetic controllers or agents;

plant disease control agents include fungicides, viricides, timber preservatives and bactericides; and soil improvement agents include fertilisers, trace metal additives, bacterial action control stimulants and soil consolidation agents.

Human and animal health or growth promoting products may be defined as any of the above intended for general health purpose, including vitamins, nutrients, steroids, and the like.

Preferred human and animal growth promoting, structural or cosmetic products as defined above include the class of appetite derivatives, for example calcium hydroxyapatite which functions as a bone or dental component, silicon which functions as a tissue modelling component, and analogues, precursors or functional derivatives thereof, bioactive species such as collagen, bioglasses and biocerseics, and components adapted for incorporation as implants into meniscus, cartilage, tissue and the like and preferably promote growth, modelling, enhancing or reinforcing of collagen, fibroblasts and other natural components of these host structures.

Absorbent biofunctional materials for poisons, toxins and the like may be defined as any natural or synthetic products capable of immobilising by absorption, interaction, reaction or otherwise of naturally occurring or artificially introduced poisons or toxins.

The biofunctional material may be in any desired form suited for the function to be performed, for example in solid, semi-solid such as thixotrope or gel form, semi-fluid or fluid such as paste of liquid form, and may be miscible, immiscible, soluble or insoluble in the polymer and/or supercritical fluid. It may be convenient to adapt the biofunctional material form to render it in preferred form for processing and the function to be performed. The material is preferably in the form of solid particles having particle size selected according to the desired application. Preferably particle size is of similar or of lesser order to that of the composition form, and optionally of any pores, preferably $10^{-9}$m–$10^{-2}$m, for example of the order of nanometers, micrometers, millimetres or centimetres. Prolonged release of material substrate may be obtained with use of relatively larger pellets of monoliths, compared with rapid release obtained with relatively smaller particles, for example.

A fluid as hereinbefore defined may comprise any known fluid which may be brought into supercritical state as commonly known in the art. As is known in the art such fluids may be subjected to conditions of temperature and pressure up to a critical point at which the equilibrium line between liquid and vapour regions disappears. Supercritical fluids are characterised by properties which are both gas like and liquid like. In particular, the fluid density and solubility properties resemble those of liquids, whilst the viscosity, surface tension and fluid diffusion rate in any medium resemble those of a gas, giving gas like penetration of the medium Preferred fluids include carbon dioxide, di-nitrogen oxide, carbon disulphide, aliphatic $C_{2-10}$ hydrocarbons such as ethane, propane, butane, pentane, hexane, ethylene, and halogenaed derivatives thereof such as for example carbon tetrafluoride or chloride and carbon monochloride trifluoride, and fluoroform or chloroform $C_{6-10}$ aromatics such as benzene, toluene and xylene, $C_{1-3}$ alcohols such as methanol and ethanol, sulphur halides such as sulphur hexafluoride, ammonia, xenon, laypton and the like. Typically these fluids may be brought into supercritical conditions at temperature of between 0–300° C. and pressures of 7–1000 bar, preferably 12–800 bar. It will be appreciated that the choice of fluid may be made according to its properties, for example diffusion and as solvent. Preferably the fluid acts as solvent for residual components of a polymer composition as hereinbefore defined but not for biofunctional material as hereinbefore defined. Choice of fluid may also be made with regard to critical conditions which facilitate the commercial preparation of the polymer as hereinbefore defined.

Preferably the fluid comprises carbon dioxide optionally in admixture with any further fluids as hereinbefore defined or mixed with conventional solvents, so-called "modified".

In a further aspect of the invention there is provided a composition comprising biofunctional polymer substrate and a biofunctional mad substrate adapted or use in or in association with the human or animal body, or cultivated or uncultivated living matter, wherein the biofunctional material substrate is optionally substantially insoluble in the polymer substrate and/or in a supercritical fluid, the polymer composition being obtained by blending substrates in a supercritical fluid and isolation thereof, in the form of a solid admixture comprising the biofunctional material substrate in substantially unchanged chemical form, and optionally in substantially unchanged physical form in the biofunctional polymer substrate.

The polymer composition may be in desired form suitable for the hereinbefore mentioned uses. For application to living matter, the polymer composition may be introduced as a dry or wet spray, powder, pellets, granules, monoliths and the like, comprising the biofunctional material substrate in releasable manner by dissolution, evaporation or the like, for example in the hereinbefore defined agrochemical, insecticidal and the like uses. For administration as a healthcare, pharmaceutical or the like biofunctional composition to the human or animal body, the composition may be suitably formulated according to conventional practices.

For use as pharmaceutical and veterinary products fabricated using the inventive process compositions may comprise creams, gels, syrups, pastes, sprays, solutions, suspensions, powders, microparticles, granules, pills, capsules, tablets, pellets, suppositories, pessaries, colloidal matrices, monoliths and boluses and the like, for administration by topical, oral, rectal, parenteral, epicutaneous, mucosal, intravenous, intramuscular, intrarespiratory or like application routes.

For use as barrier agents for human or animal or living matter, the composition may be in a suitable form comprising the biofunctional material substrate homogeneously distributed throughout the polymer matrix, which may be shaped or impregnated into a shaped product to provide the product in the form of a barrier film, layer, clothing or sheet adapted to enclose or otherwise surround the body or matter to be protected.

For use as a structural components, for example comprising the polymer and optional additional synthetic or natural metal, plastic, carbon or glass fibre mesh, scrim, rod or like reinforcing for medical or surgical use, the composition may be adapted for dry or wet insertion into a desired host structure, for example may be in powder, pellet, granule or monolith form suited for insertion as a solid monolith into bone, as fillers or cements for wet insertion into bone or teeth or as solid aggregates or monoliths for orthopaedic implants such as pins, or dental implants such as crowns etc.

Preferably a composition for staged release of material substrate may comprise one or more biofunctional material substrates as hereinbefore defined as one or more layers, obtained by repeating the process of the invention as hereinbefore defined, or by coating of the composition by conventional means.

The polymer composition may be of any desired article size in the range of sub micron powders up to monoliths of the order of centimetres magnitude. It is a particular advantage of the present invention that the polymer composition is obtained in the desired form in uniform size particles such as powder, pellets and the like. Accordingly if it is desired to obtain a random or discrete distribution of particle size the polymer composition may be milled or may be blended from different size batches.

Particle size may be controlled according to known techniques by controlled removal of supercritical fluid. If it is desired to obtain particulate composition, the process mixture is suitably removed from the mixing chamber under supercritical conditions into a separate container under subcritical conditions through a nozzle or like orifice of desired aperture, under desired difference of conditions and removal rate, adapted to provide the desired particle size. Spray drying apparatus and techniques may commonly be employed for the technique. It is a feature of the uniform solid admixture obtained in the processing stage and the uniform distribution of the suitable supercritical fluid throughout the admixture that is responsible for uniform particle size in the final polymer composition product. Non Newtonian fluids that give low viscosity enabling flow through pipes/orifices and shear thinning are particularly appropriate.

If it is desired to obtain a polymer composition in the form of monoliths, the supercritical fluid is suitably removed using known techniques for foaming polymers. Accordingly the polymer mix is retained in a mixing vessels and conditions are changed from supercritical to subcritical at a desired rate to cause removal of the fluid from the polymer mix. Depending on the nature of the polymer it is possible to obtain the monolith in porous foamed state, having interconnecting pores and channels created by the removal of the supercritical fluid, simply by selecting a polymer consistency which is adapted to retain its foamed state.

Alternatively a less viscous polymer consistency may be employed whereby a substantially non foamed or nonporous monolith may be attained by relaxation of polymer mix subsequent to removal of supercritical fluid.

Monoliths may be formed into desired shape during the processing thereof, for example by removal of supercritical fluid from a mixing vessel having the desired monolith shape. Alternatively monolith may be removed from the mixing vessel and cut to desired shape.

It is a particular feature of the invention that properties of polymer density and porosity and biodegradability may be employed to beneficial effect in release of biofunctional material substrate, such as drugs and the like in/or in association with the human or animal body or living matter, and/or as structural implants in or in association with the human or animal body or living matter, to be compatible in Terms of structural properties of the locus of implantation The nature and form of composition may also be selected according to desired loading of polymer with a biofunctional material substrate. It has been found that biofunctional material substrate may be introduced up to a maximum loading at which cohesion of polymer is no longer effective. Advantageously it has been found that higher loading may be obtained according to the process of the present invention than with known processes, by virtue of the uniform morphology of biofunctional polymer and material substrates, and loadings of biofunctional material substrate up to and in the range 0.01–99.9%, for example in excess of 50 wt %, or fin excess of 80 wt % have been obtained.

Accordingly the polymer composition of the invention may be characterised by the morphology obtained and which may be determined by analysis of a cross section thereof.

Additional components which may be incorporated during the manufacture of the polymer composition, for example initiators, accelerators, hardeners, stabilisers, anitioxidints, adhesion promoters, fillers and the like may be incorporated within the polymer. Markers and tags and the like may be incorporated to trace or detect administration or consumption of the composition according to known techniques.

If it is desired to introduce an adhesion promoter into the polymer composition, the promoter may be used to impregnate or coat particles of biofunctional material prior to production into the polymer composition, by means of simple mixing, spraying or other known coating steps, in the presence or absence of fluid as hereinbefore defined. Preferably coating is performed in conjunction with mixing with fluid as hereinbefore defined whereby excellent coating is obtained. For example the adhesion promoter is dissolved in fluid as hereinbefore defined and the solution is contacted with biofunctional material particles as hereinbefore defined. Alternatively the adhesion promoter is introduced into the autoclave during the mixing and/or polymerisation step whereby it attaches to the biofunctional material particles in desired manner.

Preferably the total amount of fillers including the biofunctional material lies in the region of 0.01–99.9 wt %, preferably 0.1–99 wt %, more preferably in excess of 50 or 60 wt %, up to for example 70 or 80 wt %.

The biofunctional material may be treated prior to or during the incorporation in the polymer with any suitable materials adapted to enhance the performance or mechanical properties thereof. The biofunctional material may be treated with components such as binders adapted to promote adhesion of material to the polymeric substrate, dispersants to increase dispersion throughout the substrate and prevent aggregate formation, to increase dispersion as a suspension throughout a supercritical fluid, activators to accelerate any biofunctional effect in situ and the like. Preferably a biofunctional material comprising hydroxapatite may be treated with binding species such as silanes and the like to facilitate increased adhesion of particles to the polymeric substrate.

Without being limited to his theory it is thought that the adhesion promoter attaches to the biofunctional material thereby exposing or otherwise selecting a binding site which may bind to the polymer or components.

Preferably the adhesion promoter is soluble in fluid as hereinbefore defined whereby residual promoter which is not bound to the biofunctional material or to the polymer is removed by extraction from the product polymer by the fluid, or the vented gas.

In a further aspect of the invention there is provided a resin, fluid or biofunctional material as hereinbefore defined or components thereof for use in the preparation of a polymer composition as hereinbefore defined.

In a further aspect of the invention there is provided an apparatus for use in the preparation of a biofunctional polymer as hereinbefore defined. Suitably the apparatus comprises one or more pressure vessels adapted for temperature and pressure elevation and comprising means for mixing the contents. The pressure vessel may include means for depressurisation or for discharging of contents into a second pressure vessel at lower pressure. The apparatus comprises means for introduction of reactants and components whilst the vessel is pressurised, as commonly known in the art.

In a further aspect of the invention there is provided a composition as hereinbefore defined for use as hereinbefore defined, for example as a pharmacologically active product, preferably a pharmaceutical or veterinary product, a human or animal health or growth promoting, structural or cosmetic product, an agrochemical or crop protection product, a natural or synthetic barrier capable of immobilising naturally ocurring or artificially introduced poisons, toxins and the like by absorption, interaction, reaction and the like.

Suitably dry or wet insertion into a human or animal host structure is by any known technique, for example for bone, implanting in orthopaedic and prosthetic applications, implanting as cement or crown in dental applications or dental restructuring, or implanting into a host structure as a slow release implant. The use of the polymer may be for cosmetic/aesthetic or for medical application. It is a particular advantage that a polymer as hereinbefore defined comprising biofunctional material may be inserted in known manner to encourage growth within the host structure whereby the insert becomes integral with the host structure.

Suitably use for release of biofunctional material as hereinbefore defined is by introducing the composition into a desired locus A. non-biodegradable polymer composition may provide release of substrate by delayed water penetration, restricted rates of substrate diffusion through voids in the polymer matrix and the like, with excretion or surgical removal of matrix from the human or animal body, or removal from any locus as desired. A biodegradable substrate may provide release in the course of biodegradation, by progressively exposing substrate to the locus with progressive degradation.

The invention is now further described with reference to specific embodiments.

In a first specific embodiment there is provided a biofunctional polymer matrix comprising biofunctional material which is substantially soluble or insoluble in a supercritical fluid wherein the polymer is of varied porosity whereby the biofunctional material is distributed throughout relatively smaller and relatively larger pores in manner to become embedded in the walls of smaller and larger pores. This may also be termed particulate morphology.

Advantageously the polymer matrix of the invention is characterised by improved mechanical properties facilitating commercial processing and additionally providing both mechanical strength and flexibility for commercial applications. In a further advantage the polymer is adapted to mimic the structure of porous human and animal host structures such as bone, meniscus and cartilage, dental and tissue structures thereby enhancing its suitability as structural or release implant and simultaneously improving biocompatibility thereof.

The polymer mar as defined above provides pores of at least two different orders of magnitude, for example of micro and macro type, each present in an amount of between 1 and 99% of the total void fraction of the polymer.

The desired orders of magnitude of the at least two pore types may be selected according to the desired application and specifically according to the host system into which it is desired to implant the polymer. Likewise, the distribution of pores of micro and macro type may be selected according to the desired applications and specifically according to the desired properties of mechanical strength and void fraction of the host system into which it is desired to implant the polymer.

The biofunctional martial is adapted to be retained within the polymer, within a host structure either temporarily or permanently. For example the material may comprise a "skeleton" which becomes integrated within the host, or may be released over a desired period, within the host structure to affect the functioning of the host structure or the body in general. In each case the polymer may optionally comprise a polymer selected from any known polymers which are adapt to degrade in the human or animal body in non-toxic manner.

In the specific embodiment the biofunctional material may comprise a biofunctional material which is selected from a component, or precursor, derivative or functional analogue thereof, of a host structure into which implantation is desired.

In this case the micro pores are suitably of a magnitude and distribution whereby embedding with biofunctional material provides an acceptable degree of biofunctionality without prejudice to the mechanical properties of the polymer. Without being limited to this theory it is thought that a fine network of biofunctional martial created in this manner may enhance the biomechanical properties of the polymer, in contrast to that of known polymers comprising inhomogeneous distribution and large aggregates of inorganic materials. For example, for orthopaedic or dental application, by embedding with an appetite component as biofunctional material a bone "skeleton" is synthetically created.

Similarly the macro pores, are suitably of magnitude and distribution whereby embedding of pore walls with a biofunctional material creates biofunctional pores mimicking those of the host structure, thereby providing by synthetic means an implant or the like which is functionally identical to the natural host In the specific embodiment the biofunctional material may otherwise comprise a pharmaceutically effective agent selected from any known agent which it is desired to release into the human or animal body by slow release means.

In this case the micro pores are suitably of magnitude and distribution whereby embedding with pharmaceutically effective agent provides a reservoir of agent, adapted for uniform or controlled slow release by means of diffusion from or biodegrading of the polymer, without prejudice to the mechanical properties of the polymer.

Similarly the macro pores are suitably of magnitude and distribution whereby embedding with a pharmaceutically effective agent to a desired thickness creates release loci into which pharmaceutically active agent may dissolve and be released, and optionally at the walls of which the degrading of biodegradable polymer takes place.

Reference herein to micro and macro pores being of different orders of magnitude is therefore to be understood to be respectively of any unit dimension and its corresponding $10^n$ multiple. For example micro pores may be of the order of $10^{-(10-7)}$m with respective macro pores of the order of $10^{-(7-5)}$m, preferably $10^{-(8-7)}$m and $10^{-(6-5)}$m respectively, more preferably of micron and $10^2$ micron order. The pores may be of any desired configuration Preferably the pores form a network of tortuous interlinking channels, more preferably wherein the micro pores interlink between the macro pores.

In a further specific embodiment of the invention the polymer resin system may comprise a residual amount of (co-) monomers, (co-) oligomers and/or pre-polymers which may be dissolved in a supercritical fluid.

Accordingly in the further specific embodiment of the invention there is provided a process for the preparation of a biofunctional polymer composition as hereinbefore defined comprising: in a first step obtaining substrates as hereinbefore defined under conditions of temperature and/or pressure to bring the fluid into supercritical state in a second step mixing thereof; and in a third step releasing the fluid in sub or super critical state under sub or super critical conditions of temperature and/or pressure whereby an amount of (co-) monomers, (co-) oligomers and/or pre-polymers dissolved in the fluid are removed from the system and the soluble or insoluble biofunctional material substrate is deposited distributed throughout the composition.

It is a particularly surprising feature of the invention that the process is independent of and may even benefit from by the presence of, or addition of, residual (co-) monomers and the like, whereas conventionally these are to be avoided for purity and toxicity reason In a further aspect of doe specific embodiment of the invention there is provided a resin system which may be cured to comprise a polymer as hereinbefore defined comprising (co-) monomers, (co-) oligomers, pre-polymers and mixtures thereof in admixture with a fluid solution or a fluid dispersion of biofunctional material in supercritical state or adapted to be brought into supercritical state in situ, wherein an amount of the (co-) monomers, (co-) oligomers and/or pre-polymers is soluble in the fluid in supercritical state and wherein the biofunctional material, as hereinbefore defined is substantially insoluble in the fluid in one or both of its super and subcritical states.

In a further aspect of the specific embodiment of the invention there is provided a cured or partially cued or otherwise non-fluid resin system for the preparation of a polymer as hereinbefore defined comprising an amount of residual (co) monomers, (co-) oligomers and/or pre-polymers in admixture with a fluid solution or fluid dispersion of a biofunctional material as hereinbefore defined in supercritical sat or adapted to be brought into supercritical state whereby the residual components are soluble in the fluid.

The invention is now illustrated in non limiting manner with reference to the following examples and Figures.

EXAMPLE 1

Polymeration to form gel with homogeneously dispersed inorganic biofunctional material—subsequent extraction of soluble monomeric/oligomeric residues by supercritical fluid processing.

Starting materials are methyl methacrylate monomer and hydroxyapatite powder at 50% by volume. The materials are mixed under constant stirring and initiator (AIBN) is added. Heating to >65° C. initiates polymerisation process and the polymerisation reaction is quenched by cooling when thickening to a gel is observed at ca 75–90% conversion to polymer under conditions employed ($M_w$>20,000).

The polymerised material is then removed from the reaction vessel and placed within a high pressure autoclave. Extraction with supercritical carbon dioxide (3000 psi/35° C.) for a period of 30 minutes at a flow rate of 1–10 ml/minute leads to removal of all $CO_2$ soluble materials namely residual monomer/low molecular weight oligomer, unreacted initiator and initiator by-products.

Figure 1B:
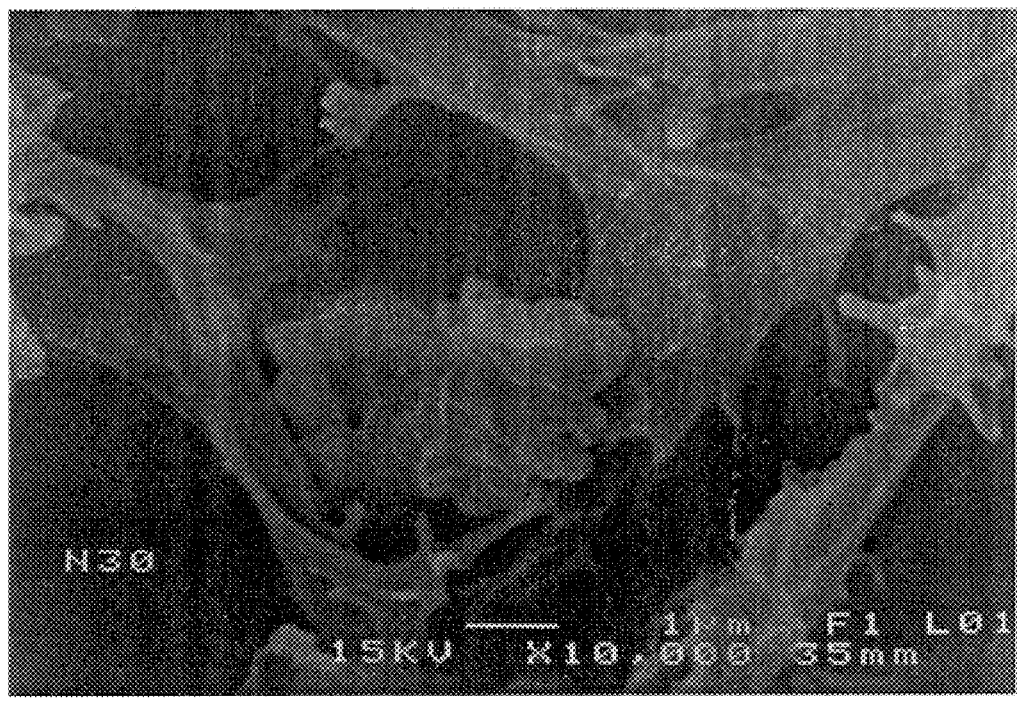
Figure 2A:
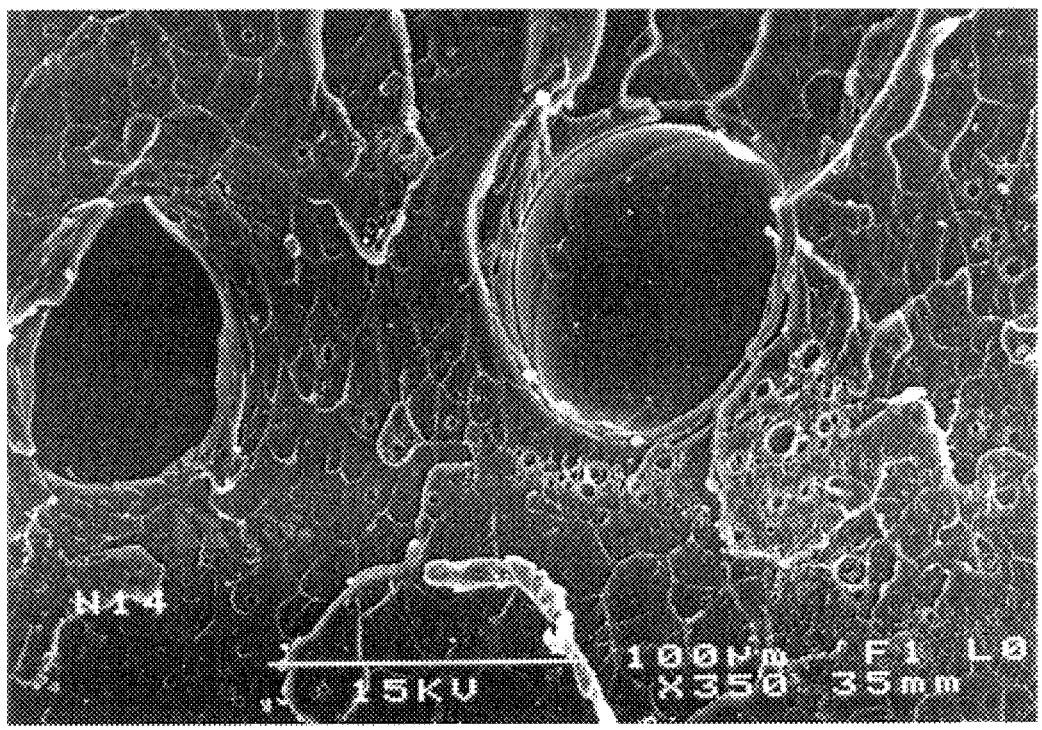
Figure 2B:
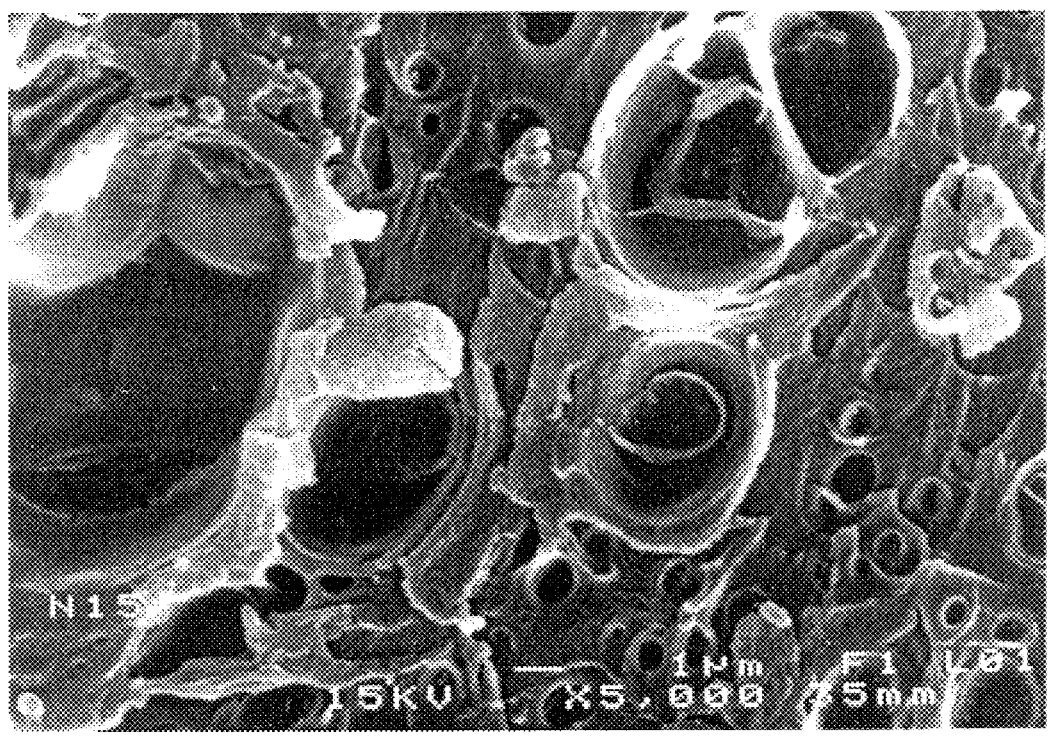

Depressurisation of autoclave leads to a porous material having 50 vol % hydroxyapatite distributed within the pores. The polymer is shown in FIGS. 1a) and 1b) which are scanning electron microscopy images at respective magnifications of 100 micron (macro pore "channel" visible) and 1 micron (micro pore "skeleton" visible). The hydroxyapatite is clearly seen uniformly distributed throughout the polymer and open porous structure, embedded in the walls of the pores in FIG. 1a) and in the form of particles trapped within the polymer substrate in the open porous structure in FIG. 1b). By comparison with FIG. 2a) (macropore "channels") and 2b) ("micropore " skeleton") the corresponding structures are shown, prepared from pure PMMA polymer by supercritical fluid processing (sc $CO_2$, 3000 psi/50° C.) without incorporation of hydroxyapatite.

EXAMPLE 2

Mixing and polymerisation step to be carried out in supercritical carbon dioxide environment.

Methyl methacrylate monomer and hydroxyapatite are added to a high pressure autoclave. The autoclave is equipped with highly efficient stirring and temperature control. The autoclave is charged with carbon dioxide at a defined temperature and pressure (ca. 75° C., 3000 psi). The vessel is charged with initiator (AIBN) and polymerisation occurs leading to hydroxyapatite encapsulated in a polymeric foam The pressure and temperature of the vessel are controlled so as to ensure density matching of carbon dioxide solvent and the polymer and efficient stirring leads to homogeneous mixing of hydroxyapatite.

Discharging of the contents into a second autoclave at lower pressure yields a homogeneous porous powder of hydroxyapatite encapsulated in polymer.

EXAMPLE 3

As in Example 2. But starting with polymer or high molecular weight oligomer and HA powder. The autoclave is charged with carbon dioxide at a defined temperature and pressure (ca. 75° C., 3000 psi), sufficient to ensure density matching of carbon dioxide solvent and polymer. Discharging of the contents into a second autoclave at low pressure yields a homogeneous porous powder of hydroxyapatite encapsulated in polymer.

EXAMPLE 4

SCF use in Pharmaceutical Manufacturing

Figure 3A:
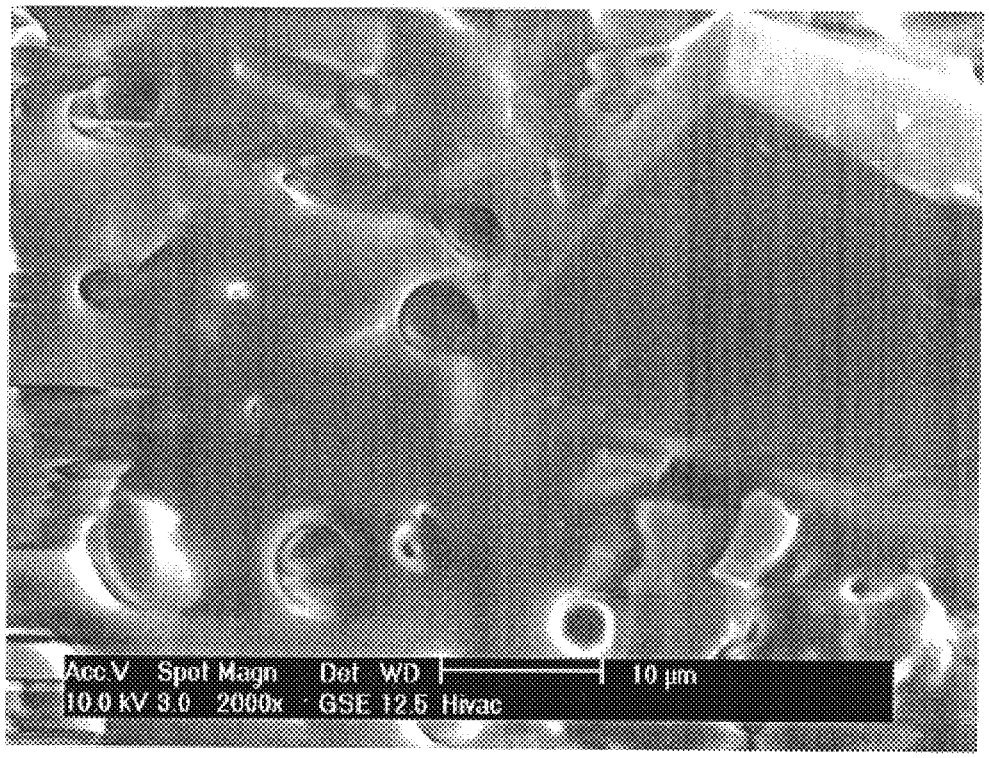
Figure 3B:
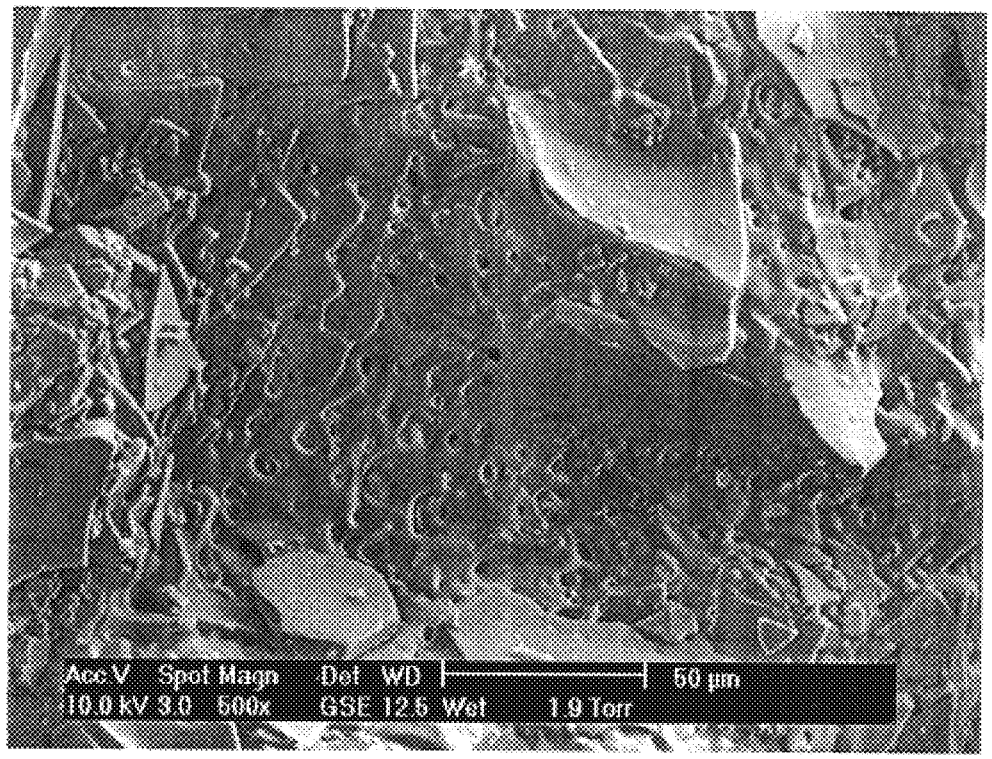

In a specific example of the use of the invention particles of the protein catalase (ca mean diameter 50 micron) are mixed with the biodegradable polymer poly(DL-lactide-co-glycolide) (PLGA) as per example 3, in the presence of super critical CO2 at 45° C. and 200 bar. After agitation for 30 minutes, the autoclave was depressussed leading to solid dispersions of a monolith form, in which catalase particles are intimately mixed with the biodegradable polymer. FIG. 3a) and 3b) are scanning electron microscopy images at respective higher and lower magnifications of 10 micron (particles and micropores visible) and 50 micron (particles embedded in "channels").

The percentage incorporation of the catalase into the biodegradable matrices was determined by the weight ratio of the catalase:PLGA. Incorporation values of between 1 and 50% were routinely manufactured.

Removal of the catalase from the matrices by degradation of the polymer enabled the activity of the enzyme to be quantified using a hydrogen peroxide decomposition assay. The results of this assay demonstrated that the enzyme lost no appreciable activity due to the SCF processing.

Such dispersions may be employed as controlled drug delivery devices that release catalase at rates determined by the porosity of the polymer matrix or the PLGA:catalase ratio.

EXAMPLE 5

Method for producing monoliths or non-powdered composite materials

As in Examples 2 and/or 3 leading to a homogenised foam structure within the primary autoclave. In this case stirring is ceased and the autoclave is depressurised leading to a foamed block of composite material. Further processing (extraction, further polymerisation and cross-linking) is performed as required.

EXAMPLE 6

As in Example 2, 3, 5 but allowing for addition of a binding species (gamma-methacryloxypropyltrimethoxysilane) to facilitate increased adhesion of apatite particles to the polymeric substrate. The (gamma-methacryloxypropyltrimethoxysilane) species is soluble in supercritical $CO_2$ and may be injected into the autoclave during the mixing and/or polymerisation step. The siloxane group attaches to the hydroxy apatite leaving a free acrylate group which may be incorporated into the polymeric substrate.

Alternatively, the hydroxyapatite particles may be pretreated with such a species prior to mixing. Pre-treatment may be performed by a supercritical coating step. Dissolution of the siloxane binder in supercritical $CO_2$ and subsequent exposure of the hydroxyapatite particles leads to coating of the HA particles. These particles may then be treated as per examples 2, 3, 5.

The solubility of this binder in $CO_2$ ensures that residual material, not bound to the HA or the polymer substrate is removed from the final product.

It will be apparent from the examples that the process of the invention achieves highly satisfactory removal of residual monomers and the like. This is of particular advantage for toxicity purposes, whereby release of monomers and the like into the human or animal body is highly undesirable and is to be avoided.

It will also be apparent from the examples that the choice of a polymer for use in preparing biofunctional polymers of the invention may be distinct from chosen for preparation of such materials by conventional technique. In particular, certain polymers such as polyethylene may be preferred for conventional biofunctional polymer preparation, in view of the fact that the amount of monomer residues (ethylene) is minimal, thereby minimising the toxic effects of the polymer. It will be apparent from the foregoing that it may in some cases be tolerated or even desirable to select a polymer composition having an amount of monomer residues and the like, or to introduce such residues whereby beneficial effects may be obtained, for example the desired porosity may be obtained by removal of monomers with the fluid or vented gas.

Further aspects and advantages of the invention will be apparent from the foregoing.

What is claimed is:

1. A process for the preparation of a composition comprising a solid admixture of a biofunctional polymer substrate and a biofunctional material substrate for use in or in association with the human or animal body, cultivated or uncultivated living matter, which process comprises contacting a mixture of the substrates or their precursors with a supercritical fluid under supercritical conditions of reduced viscosity to plasticise and swell the biofunctional polymer substrate and under conditions of physical blending to distribute the biofunctional material substrate throughout the biofunctional polymer substrate, and releasing the supercritical fluid under subcritical conditions, wherein the biofunctional material substrate retains bioactivity in the solid admixture.

2. The process according to claim 1, wherein the precursors react to form the biofunctional polymer substrate, the biofunctional material substrate, or both in situ.

3. The process according to claim 1, wherein the solid admixture comprises the biofunctional material substrate encapsulated by the biofunctional polymer substrate in the form of a coating, non-uniformly distributed throughout the polymer as a particulate morphology or intimately admixed and uniformly distributed throughout the biofunctional polymer substrate as a (co-) continuous morphology.

4. The process according to claim 1, wherein the process comprises mixing the biofunctional material substrate in solid phase and in the absence of a solvent or a carrier into the biofunctional polymer substrate in a fluid phase or a solid phase and the supercritical fluid.

5. The process according to claim 1, wherein the conditions of reduced viscosity and physical blending comprise agitation with associated shear thinning.

6. The process according to claim 1, wherein temperature and pressure are controlled to provide density matching of the supercritical fluid and the biofunctional polymer substrate.

7. The process according to claim 1, wherein releasing the supercritical fluid under subcritical conditions is achieved in situ by depressuring a pressure vessel in which the process is carried out.

8. The process according to claim 1, wherein the biofunctional polymer substrate is non-toxic to humans and animals.

9. The process according to claim 1, wherein the biofunctional material substrate is selected from the group consisting of bioactive materials, bioinert materials, and biocidal materials.

10. The process according to claim 9, wherein the biofunctional material substrate is a pharmacologically active compound selected from the group consisting of: pharmaceutical products; veterinary products; human and animal health products; growth promoting, structural, and cosmetic products; agrochemical and crop protection products; natural and synthetic barriers for immobilising poisons and toxins by absorption, interaction, and reaction.

11. The process according to claim 1, wherein the supercritical fluid is selected from the group consisting of carbon dioxide, di-nitrogen oxide, carbon disulphide, aliphatic $C_{2-10}$ hydrocarbons, halogenated $C_{2-10}$ hydrocarbons, $C_{6-10}$ aromatics, $C_{1-3}$ alcohols, sulphur halides, ammonia, xenon, and krypton brought into supercritical conditions at a temperature of between 0–300° C. and a pressure of between 7–1000 bar.

12. The process according to claim 1, wherein releasing the supercritical fluid under subcritical conditions is achieved ex situ by discharging the contents of a pressure vessel in which the process is carried out.

13. A composition made by the process of claim 1.

14. The composition according to claim 13, wherein the biofunctional polymer substrate and the biofunctional material substrate are present in the form of particles of uniform or random particle size or distribution thereof.

15. The composition according to claim 13, wherein the biofunctional polymer substrate and the biofunctional material substrate are present in the form of shaped or unshaped monoliths.

16. The composition according to claim 13 in a formulation for topical, oral, rectal parenteral, epicutaneous, mucosal, intravenous, intramuscular, or intrarespiratory administration.

17. A composition according to claim 13, wherein the biofunctional polymer substrate and the biofunctional material substrate are present as a solid admixture within individual particles of particle size from submicron range powders to monoliths in centimeter range.

18. The composition according to claim 13, which comprises one or more layers of at least one biofunctional material substrate, wherein the biofunctional material substrate is (staged) released by delayed water penetration or by restricted rates of substrate diffusion through voids in the biofunctional polymer substrate in the course of biodegradation.

19. The composition according to claim 13, comprising the biofunctional material substrate in loading of 0.01 to 99.9 wt %.

20. The composition according to claim 13, wherein the composition is pharmacologically active and is a pharmaceutical product, a veterinary product, a human health product, an animal health product, a growth promoting, structural or cosmetic product, an agrochemical or crop protection product, or a natural or synthetic barrier for immobilising poisons and toxins.

21. The composition according to claim 16, wherein the formulation is a cream, a gel, a syrup, a paste, a spray, a solution, a suspension, a powder, a microparticle, a granule, a pill, a capsule, a tablet, a pellet, a suppository, a pessary, a colloidal matrix, a monolith, or a bolus.

22. The composition according to claim 16, which further comprises a reinforcing structure selected from the group consisting of metal, plastic, carbon, or glass.

23. The composition according to claim 16, wherein the composition may be used as a filler, a cement, a solid aggregate, a monoliths pin, a crown, an orthopedic implant, a dental implant, a protective barrier, or a combination thereof.

24. A biofunctional polymer matrix comprising a solid biofunctional material substrate in a biofunctional polymer substrate and a supercritical fluid, wherein the biofunctional polymer substrate is of varied porosity whereby the biofunctional material substrate is distributed and embedded throughout the biofunctional polymer substrate.

25. The biofunctional polymer matrix according to claim 24, which provides pores of at least two different orders of magnitude present in an amount of between 1 and 99% of the total void fraction of the biofunctional polymer substrate.

26. A process for the preparation of the biofunctional polymer matrix according to claim 25 which comprises obtaining to bring the fluid into a supercritical state;

mixing the biofunctional polymer substrate, the biofunctional material substrate, and the supercritical fluid under conditions of physical blending; and releasing the fluid under conditions whereby an amount of (co-) monomers, (co-) oligomers pre-polymers, or a combination thereof dissolved in the fluid are removed and the biofunctional material substrate is distributed throughout the matrix.

* * * * *